(12) United States Patent
Thornton

(10) Patent No.: US 11,020,260 B2
(45) Date of Patent: Jun. 1, 2021

(54) NAVEL RETAINER AND RELATED TECHNIQUES

(71) Applicant: Pamela Thornton, Hooksett, NH (US)

(72) Inventor: Pamela Thornton, Hooksett, NH (US)

( * ) Notice: Subject to any disclaimer, the term of this patent is extended or adjusted under 35 U.S.C. 154(b) by 109 days.

(21) Appl. No.: 15/978,476

(22) Filed: May 14, 2018

(65) Prior Publication Data
US 2019/0008670 A1 Jan. 10, 2019

Related U.S. Application Data

(60) Provisional application No. 62/529,796, filed on Jul. 7, 2017, provisional application No. 62/531,957, filed on Jul. 13, 2017.

(51) Int. Cl.
*A61F 5/01* (2006.01)
*A61M 29/02* (2006.01)
*A44C 15/00* (2006.01)

(52) U.S. Cl.
CPC .......... *A61F 5/01* (2013.01); *A44C 15/0045* (2013.01); *A61M 29/02* (2013.01); *A61M 2205/0216* (2013.01); *A61M 2205/0272* (2013.01); *A61M 2205/07* (2013.01); *A61M 2205/10* (2013.01); *A61M 2210/10* (2013.01)

(58) Field of Classification Search
CPC ... A61F 5/01; A44C 15/0045; A44C 15/0035; A44C 7/002; A44C 7/004; A61M 29/02; A61M 2205/10; A61M 2205/07; A61M 2205/0272; A61M 2205/0216; A61M 2210/10; A61B 17/0057; A61B 2017/00637
See application file for complete search history.

(56) References Cited

U.S. PATENT DOCUMENTS 3,674,032 A 7/1972 Minganti
3,831,398 A 8/1974 Davis, Sr.
(Continued)

OTHER PUBLICATIONS

The Hillman Group, "Internal Retaining Ring—881378", https://www.homedepot.com/p/The-Hillman-Group-11-16-in-Internal-Retaining-Ring-10-Pack-881378, 2 pages.
(Continued)

*Primary Examiner* — Katherine H Schwiker
*Assistant Examiner* — Alexis D Amechi
(74) *Attorney, Agent, or Firm* — Hayes Soloway PC

(57) ABSTRACT

A navel retainer and related techniques are disclosed. The retainer may be configured to be deployed within a navel such that its body portion interfaces with tissue therein. In some embodiments, the retainer may include an adjustment mechanism configured to expand and collapse the size and, optionally, geometry of the body portion. In some embodiments, the retainer may be a resilient element, allowing it to be temporarily compressed and subsequently allowed to expand in size, in some cases also optionally changing its geometry. In either manner, the retainer may be adjusted in size and/or geometry to buttress the tissue of the navel, minimizing or otherwise reducing opportunity for navel contracture during a healing process. After a desired navel size and shape are achieved, a separate maintenance device optionally may be deployed within the navel. The retainer optionally may be configured to host or otherwise serve as a navel adornment.

20 Claims, 5 Drawing Sheets

(56) References Cited

U.S. PATENT DOCUMENTS

| | | | |
|---|---|---|---|
| 4,761,971 A * | 8/1988 | Freier | A44C 7/00 411/339 |
| 5,309,737 A * | 5/1994 | Fountoulakis | A44C 7/003 24/704.1 |
| 5,946,943 A * | 9/1999 | Hanson | A44C 17/0216 63/12 |
| 6,039,049 A * | 3/2000 | Piperato | A44C 15/0035 128/898 |
| 6,125,657 A * | 10/2000 | Esposito | A44C 7/00 24/598.2 |
| 6,470,709 B1 * | 10/2002 | Siekierski | A44C 7/003 63/12 |
| 7,875,267 B2 | 1/2011 | Okajima et al. | |
| 8,425,410 B2 | 4/2013 | Murray et al. | |
| 8,443,626 B2 | 5/2013 | Simpson et al. | |
| 8,753,355 B2 | 6/2014 | Bachmann | |
| 8,821,513 B1 | 9/2014 | Bachmann | |
| 9,066,562 B2 * | 6/2015 | Azar | A44C 17/0233 |
| 9,119,666 B2 | 9/2015 | Kleyman et al. | |
| 2002/0020190 A1 | 2/2002 | Clark et al. | |
| 2003/0040768 A1 * | 2/2003 | Greene | A61B 17/0057 606/190 |
| 2004/0093898 A1 * | 5/2004 | McConnell | A44C 15/0035 63/1.11 |
| 2004/0255620 A1 * | 12/2004 | Chuang | A44C 15/001 63/29.1 |
| 2006/0021382 A1 * | 2/2006 | Tyler | A44C 9/0038 63/12 |
| 2010/0147025 A1 | 6/2010 | Simpson et al. | |
| 2010/0180907 A1 | 7/2010 | Okajima et al. | |
| 2013/0110149 A1 | 5/2013 | Schomburg | |
| 2013/0178873 A1 * | 7/2013 | Vekios | A61B 17/0057 606/151 |
| 2013/0178885 A1 | 7/2013 | Lee | |
| 2015/0238250 A1 | 8/2015 | Kieturakis | |
| 2015/0327848 A1 | 11/2015 | Kleyman et al. | |
| 2016/0143638 A1 | 5/2016 | Renke | |
| 2016/0151195 A1 | 6/2016 | Vekios et al. | |
| 2016/0270880 A1 | 9/2016 | Hines et al. | |
| 2017/0006979 A1 * | 1/2017 | Wang | A44C 9/02 |

OTHER PUBLICATIONS

Tummy Toys, "Exclusive Platinum Belly Button Ring Sleeper", Product ID: TT-51000, http://www.tummytoys.com/group/easy-body-jewelry-quality-tummy-toys-belly-button-navel-rings-2.aspx#_i_platinum-belly-button-ring-navel-body-jewelery-sexy-easy-custom-20, 1 page.

* cited by examiner

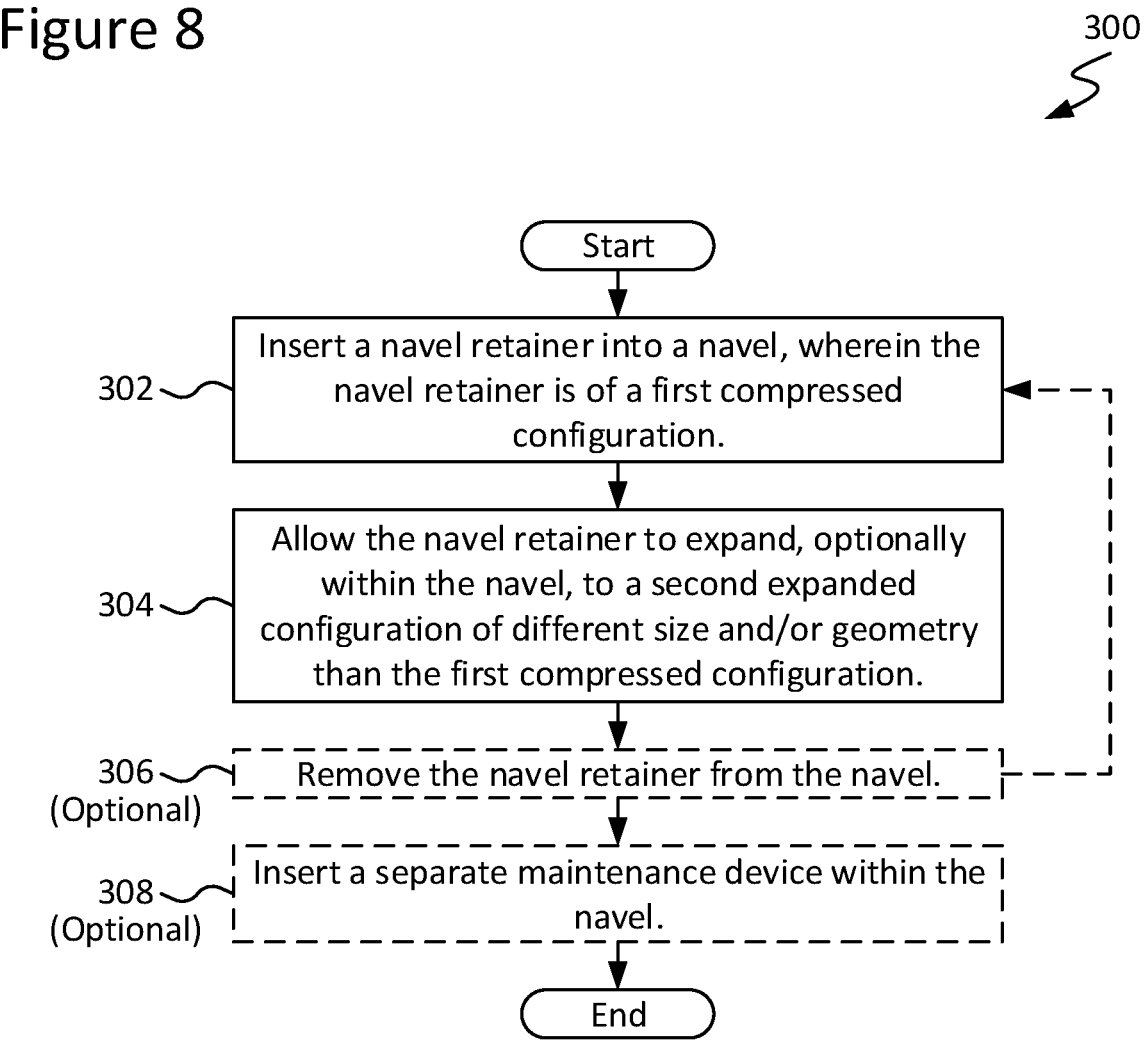

NAVEL RETAINER AND RELATED TECHNIQUES

CROSS-REFERENCE TO RELATED APPLICATIONS

This patent application claims the benefit of U.S. Provisional Patent Application No. 62/529,796, titled "Adjustable Navel Retainer and Related Techniques," filed on Jul. 7, 2017, and U.S. Provisional Patent Application No. 62/531, 957, titled "Resilient Navel Retainer and Related Techniques," filed on Jul. 13, 2017, each of which is herein incorporated by reference in its entirety.

FIELD OF THE DISCLOSURE

The present disclosure relates to medical devices and, more particularly, to a navel retainer for use in combatting navel contracture.

BACKGROUND

In placental mammals, the umbilicus, also known as the navel or belly button, is the attachment site of the umbilical cord. Navel size and shape vary from species to species and even between individual mammals of a given species. In humans, the navel normally resides on the abdomen and is generally rounded in shape. Colloquially, navels of generally concave indentation are known as "innies," whereas navels that protrude beyond the abdomen are known as "outies."

SUMMARY

The subject matter of this application may involve, in some cases, interrelated products, alternative solutions to a particular problem, and/or a plurality of different uses of a single system or article.

One example embodiment provides a navel retainer device. The navel retainer device includes: a body portion configured to interface with tissue of a navel hosting the navel retainer device; and an adjustment mechanism configured to adjust at least one of a size and a geometry of the body portion such that the body portion exerts pressure on the tissue in a manner that resists contracture of the navel. In some cases, the body portion includes: a first curved body portion; and a second curved body portion disposed opposite the first curved body portion. In some such cases, the first curved body portion and the second curved body portion are configured such that, in a fully collapsed state of the navel retainer device, the body portion is of substantially circular geometry. In some other such cases, the first curved body portion and the second curved body portion are configured such that, in a fully collapsed state of the navel retainer device, the body portion is of substantially elliptical, oval, oblate, or prolate geometry. In some instances, the navel retainer device further includes a brace portion configured to operatively couple the body portion with the adjustment mechanism. In some instances, the navel retainer device further includes a biasing member disposed between the first curved body portion and the second curved body portion, wherein the biasing member is configured to maintain orientation of the first curved body portion and the second curved body portion with respect to one another. In some cases, the navel retainer device further includes at least one intervening layer configured to be disposed between the body portion and the tissue of the navel. In some instances, the adjustment mechanism includes a threaded screw-based mechanism. In some instances, the adjustment mechanism includes a spring-based mechanism. In some instances, the adjustment mechanism includes a gear-based mechanism. In some cases, the adjustment mechanism is configured to generate movement of the body portion within the navel via at least one of a mechanical element, a hydraulic element, a pneumatic element, an electronic element, and a magnetic element. In some instances, the adjustment mechanism is configured to be adjusted manually. In some instances, the adjustment mechanism is configured to be adjusted utilizing a tool. In some cases, the navel retainer device further includes at least one of: a central ornamentation mounting portion configured to mount navel ornamentation; and a peripheral ornamentation mounting portion configured to mount navel ornamentation.

Another example embodiment provides a method of using a navel retainer. The method includes: inserting a navel retainer device into a navel, wherein the navel retainer device is initially of a first configuration; and adjusting the navel retainer device within the navel to a second configuration, wherein the second configuration is of at least one of a different size and a different geometry than the first configuration. In some cases, the navel retainer device includes: a body portion configured to interface with tissue of the navel; and an adjustment mechanism configured to adjust at least one of the size and the geometry of the body portion such that the body portion exerts pressure on the tissue in a manner that resists contracture of the navel. In some such cases, the body portion includes: a first curved body portion; and a second curved body portion disposed opposite the first curved body portion. In some cases, the adjustment mechanism includes at least one of a threaded screw-based mechanism, a spring-based mechanism, and a gear-based mechanism. In some cases, the adjustment mechanism is configured to generate movement of the body portion within the navel via at least one of a mechanical element, a hydraulic element, a pneumatic element, an electronic element, and a magnetic element. In some instances, after adjusting the navel retainer device to the second configuration, the method further includes: removing the navel retainer device from the navel. In some such instances, after removing the navel retainer device from the navel, the method further includes: inserting a maintenance device within the navel, wherein the maintenance device is configured to maintain at least one of a size and a geometry of the navel.

Another example embodiment provides a system for combating navel contracture. The system includes a first navel retainer device including: a first curved body portion; a second curved body portion disposed opposite the first curved body portion; and an adjustment mechanism configured to adjust at least one of a size and a geometry of the first navel retainer device by changing a distance between the first curved body portion and the second curved body portion. The system further includes a second navel retainer device including: a flexible body portion of open curve geometry having a gap defined therein such that the flexible body portion is discontinuous; and a biasing member disposed within the gap and configured to bias the flexible body portion to an expanded state. In some cases, at least one of the first curved body portion and the second curved body portion is semi-circular in shape. In some instances, the biasing member includes at least one of a spring, an elastomeric element, a piston, and a body capable of telescoping.

Another example embodiment provides a navel retainer device. The navel retainer device includes a resilient body portion of open curve geometry having a gap defined therein such that the resilient body portion is discontinuous, wherein: the resilient body portion is configured to interface with tissue of a navel hosting the navel retainer device; and the resilient body portion is configured to resist compression of a size thereof as well as to exert pressure on the tissue in a manner that resists contracture of the navel. In some cases, the resilient body portion is configured such that, in a fully collapsed state of the navel retainer device, the resilient body portion is of substantially circular geometry. In some other cases, the resilient body portion is configured such that, in a fully collapsed state of the navel retainer device, the resilient body portion is of substantially elliptical, oval, oblate, or prolate geometry. In some instances, the navel retainer device further includes at least one intervening layer configured to be disposed between the resilient body portion and the tissue of the navel. In some cases, the resilient body portion is configured to be compressed manually. In some cases, the resilient body portion is configured to be compressed utilizing a tool. In some instances, the navel retainer device further includes an ornamentation mounting portion configured to mount navel ornamentation.

Another example embodiment provides a method of using a navel retainer device. The method includes: inserting the navel retainer device into a navel, wherein the navel retainer device is initially of a first compressed configuration; and allowing the navel retainer device to expand within the navel to a second expanded configuration, wherein the second expanded configuration is of at least one of a different size and a different geometry than the first compressed configuration. In some cases, the navel retainer device includes a resilient body portion of open curve geometry having a gap defined therein such that the resilient body portion is discontinuous, wherein: the resilient body portion is configured to interface with tissue of the navel; and the resilient body portion is configured to resist compression of a size thereof as well as to exert pressure on the tissue in a manner that resists contracture of the navel. In some instances, after allowing the navel retainer device to expand to the second expanded configuration, the method further includes: removing the navel retainer device from the navel. In some such instances, after removing the navel retainer device from the navel, the method further includes: inserting a maintenance device within the navel, wherein the maintenance device is configured to maintain at least one of a size and a geometry of the navel.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the inventive subject matter.

BRIEF DESCRIPTION OF THE DRAWINGS

FIG. 8 is a flowchart illustrating a method of using a navel retainer in accordance with another embodiment of the present disclosure.

Figure 1:
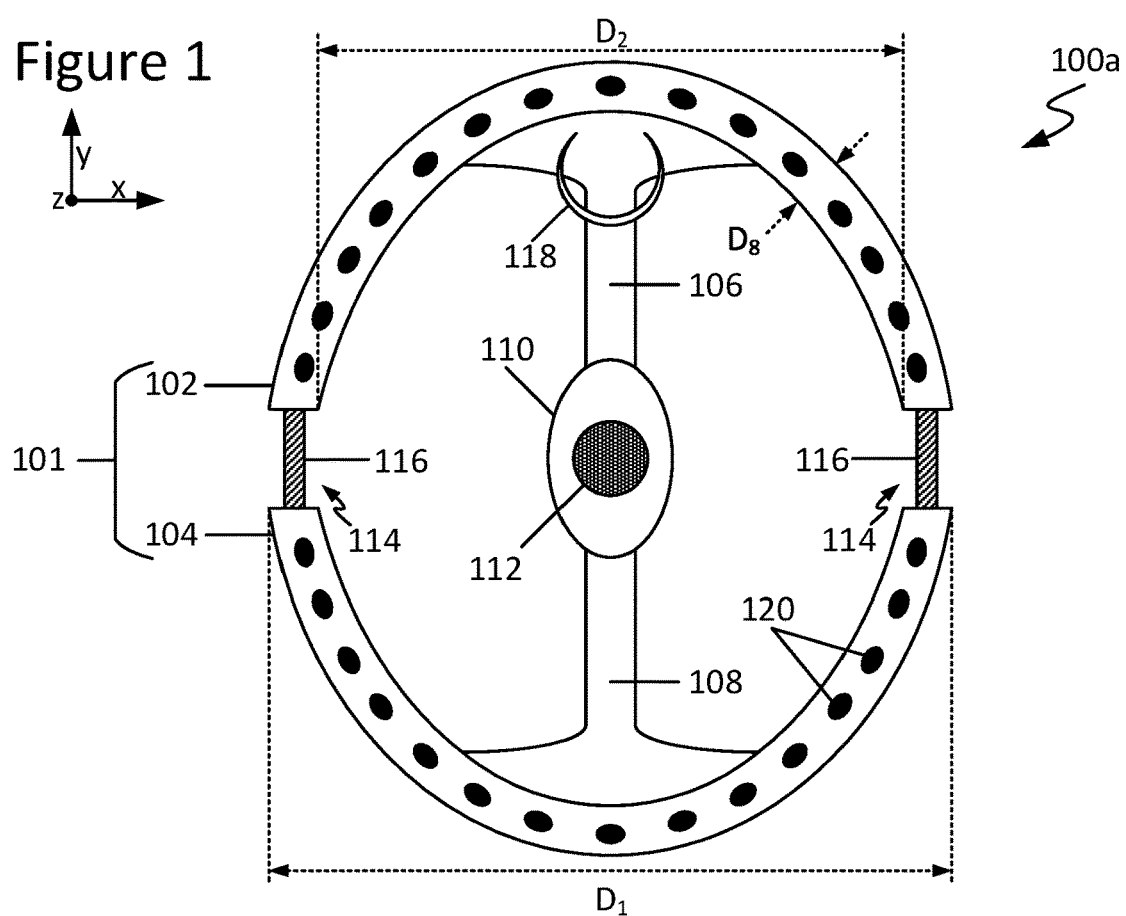
FIG. 1 illustrates a side elevation view of a navel retainer configured in accordance with an embodiment of the present disclosure.

These and other features of the present embodiments will be understood better by reading the following detailed description, taken together with the figures herein described. In the drawings, each identical or nearly identical component that is illustrated in various figures may be represented by a like numeral. For purposes of clarity, not every component may be labeled in every drawing. Furthermore, as will be appreciated in light of this disclosure, the accompanying drawings are not intended to be drawn to scale or to limit the described embodiments to the specific configurations shown.

DETAILED DESCRIPTION

A navel retainer and related techniques are disclosed. In accordance with some embodiments, the disclosed navel retainer may be configured to be deployed within a navel such that its body portion interfaces, directly or indirectly, with tissue therein. In some embodiments, the disclosed navel retainer may be configured as an adjustable element, including an adjustment mechanism configured to expand and collapse the size and, optionally, geometry of the body portion. In some embodiments, the disclosed navel retainer may be configured as a resilient element, characterizable as tending to recoil or spring back into shape despite being compressed or otherwise deflected from an undisturbed state, allowing it to be temporarily compressed and subsequently allowed to expand in size, in some cases also optionally changing its geometry. In either manner, the disclosed navel retainer may be adjusted in size and/or geometry to buttress the tissue of the navel, minimizing or otherwise reducing opportunity for contracture of the navel, for example, during the healing process. In accordance with some embodiments, after a desired navel size and shape are achieved, a separate maintenance device optionally may be deployed within the navel. In some embodiments, the disclosed navel retainer may be configured to host or otherwise serve as a navel adornment. Numerous configurations and variations will be apparent in light of this disclosure.

General Overview

Contracture of the navel may result from surgeries, pregnancy, or localized injury, among other sources. In some instances, the contracture is severe enough to cause deformity of the navel. Existing approaches to combating physiological forces involved in navel contracture include insertion and retention of a marble or a foam earplug in the navel during the healing process. However, such existing approaches are not normally permanently effective, can be undesirably noticeable under clothing or with an exposed midriff, and can lead to additional medical complications, including infection, as well as pain.

Regarding navel piercings, not every individual's anatomy may be conducive to piercing. Without a well-defined region of tissue at the navel, there is an increased chance for difficulties during the healing process after piercing, including rejection by the body. Because the tissue in the navel region may not be particularly vascular, the lesser blood flow to the area may extend the healing process. Moreover, because of its location, navel piercing sites typically are subjected to constant bending, stretching, folding, and friction, each of which can contribute to extending the healing process. Additional complications related to navel piercings may include scarring, tearing, and pain, as well as infection and blood poisoning in some cases. With the long healing time and commitment required in maintaining sanitary conditions of the piercing site, navel piercing may be a decision worthy of careful forethought.

Thus, and in accordance with some embodiments of the present disclosure, a navel retainer and related techniques are disclosed. In accordance with some embodiments, the disclosed navel retainer may be configured to be deployed within a navel such that its body portion interfaces, directly or indirectly, with tissue therein. In some embodiments, the disclosed navel retainer may be configured as an adjustable element, including an adjustment mechanism configured to expand and collapse the size and, optionally, geometry of the body portion. In some embodiments, the disclosed navel retainer may be configured as a resilient element, characterizable as tending to recoil or spring back into shape despite being compressed or otherwise deflected from an undisturbed state, allowing it to be temporarily compressed and subsequently allowed to expand in size, in some cases also optionally changing its geometry. In either manner, the disclosed navel retainer may be adjusted in size and/or geometry to buttress the tissue of the navel, minimizing or otherwise reducing opportunity for contracture of the navel, for example, during the healing process. In accordance with some embodiments, after a desired navel size and shape are achieved, a separate maintenance device optionally may be deployed within the navel. In some embodiments, the disclosed navel retainer may be configured to host or otherwise serve as a navel adornment.

In accordance with some embodiments, the disclosed navel retainer may be considered, in a general sense, a medical device configured to help keep the navel open at normal (or otherwise desired) dimensions and geometry during (and optionally after) healing of the navel and surrounding region of the abdomen. In at least some cases, the disclosed navel retainer may be utilized, for example, in post-operative care after abdominal surgery (e.g., umbilical hernia repair surgery; abdominoplasty or "tummy tuck" surgery) or during healing in the post-natal period or following a localized abdominal injury, among other scenarios. Use of the disclosed navel retainer may serve to minimize or otherwise reduce the opportunity for navel deformity to occur during such healing periods. In accordance with some embodiments, the disclosed navel retainer may be configured to provide for adjustment and progression of the size and, optionally, shape of the device, and thus the host navel, without need for using a series of individual umbilical splints of different sizes and shapes. Moreover, use of the disclosed navel retainer may be a safe and practical alternative to traditional navel piercings for users of all ages, eliminating or otherwise reducing complications normally associated therewith.

As will be appreciated in light of this disclosure, the disclosed navel retainer may be used periodically or continuously for a given period. As will be further appreciated, the adjustable nature of the disclosed navel retainer may make it ideal for use in cases of protracted healing periods and for customizable umbilicus shaping and sizing. The disclosed navel retainer also may be configured for use in conjunction with, or on its own as, navel jewelry. As will be further appreciated, the disclosed navel retainer may be configured, in accordance with some embodiments, so as not to require any bandage, wrap, tape, adhesive, or other further external element to effectuate deployment and retention in the navel. More generally, the disclosed navel retainer may be configured for deployment and retention with any umbilicus, whether protruding (e.g., an "outie") or recessed (e.g., an "innie").

Structure and Operation

Figure 2:
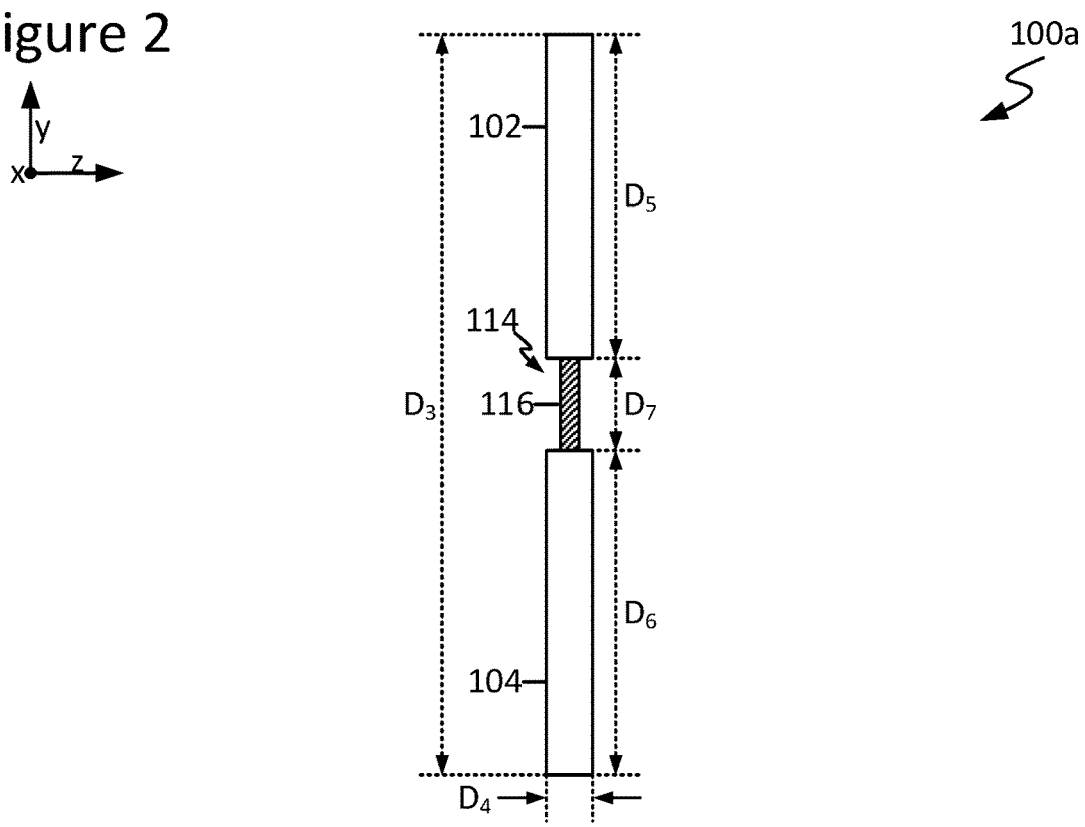
FIG. 2 illustrates another side elevation view of the navel retainer of FIG. 1.
Figure 3:
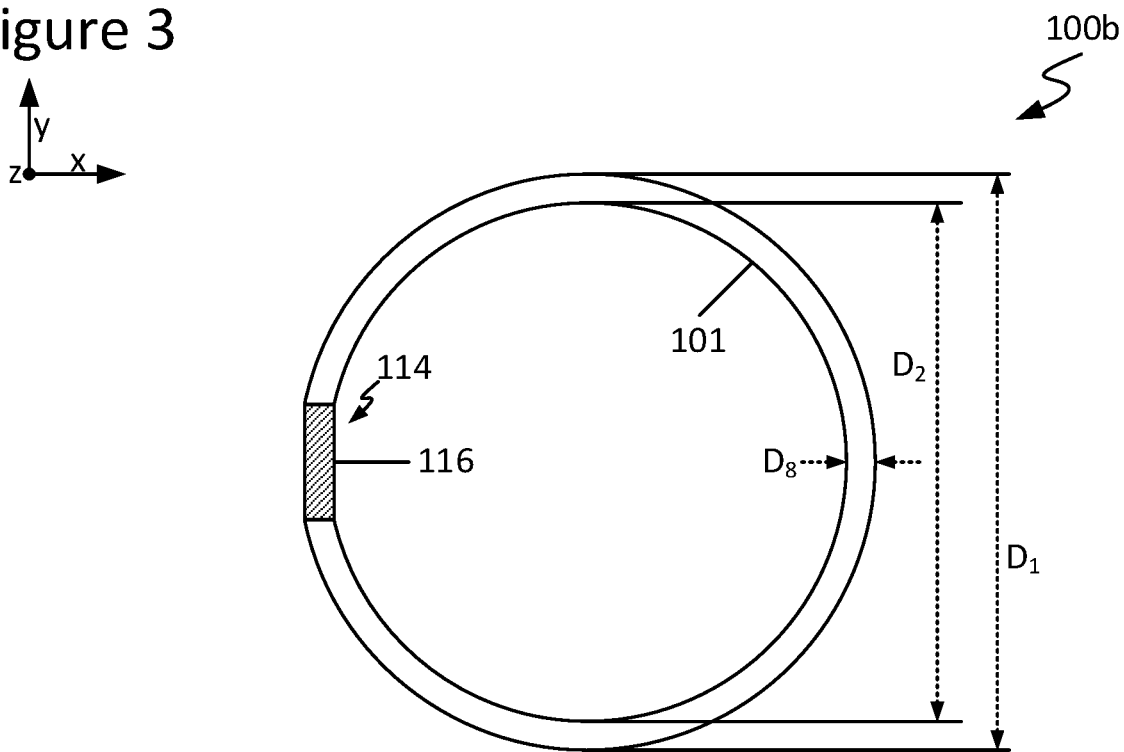
FIG. 3 illustrates a side elevation view of a navel retainer configured in accordance with another embodiment of the present disclosure.
Figure 4:
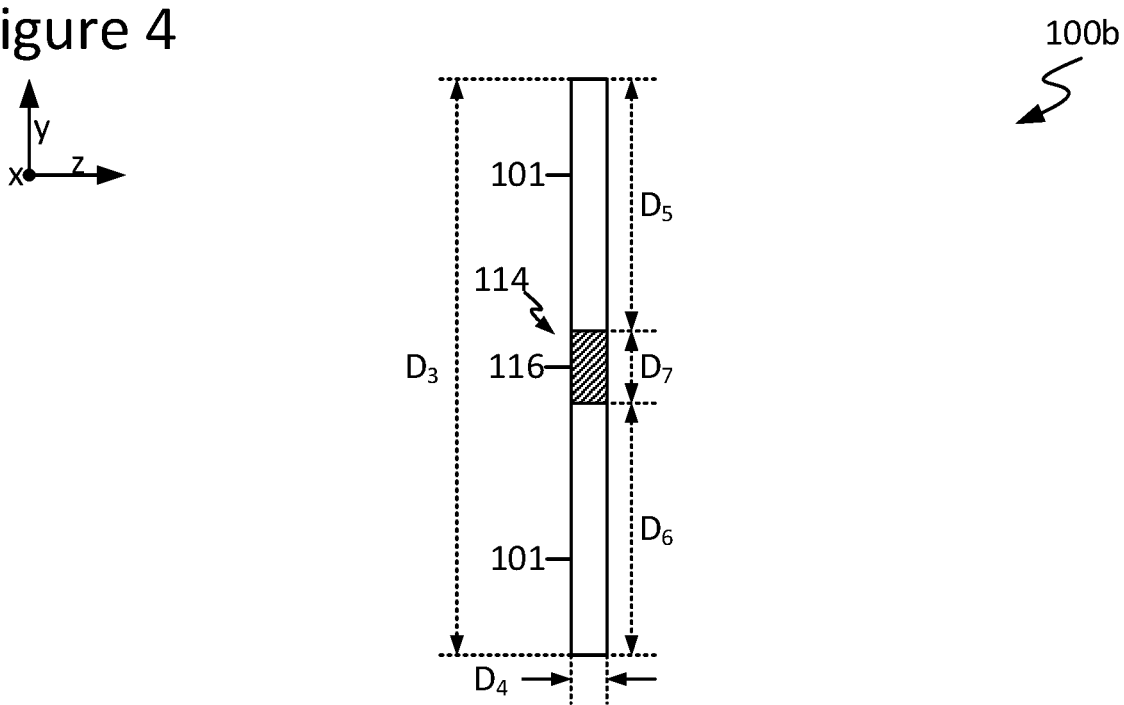
FIG. 4 illustrates another side elevation view of the navel retainer of FIG. 3.

FIGS. 1-2 illustrate several views of a navel retainer 100a configured in accordance with an embodiment of the present disclosure. FIGS. 3-4 illustrate several views of a navel retainer 100b configured in accordance with another embodiment of the present disclosure.

As can be seen, navel retainer 100a, 100b may include a body portion 101, which may be configured to interface, directly or indirectly, with the interior sidewalls of a navel. In some embodiments, such as that generally shown in FIGS. 1-2, body portion 101 may be of multi-piece construction (e.g., may constitute a polylithic element), including a first body portion 102 and a second body portion 104, which may be disposed substantially opposite one another. In some other embodiments, such as that generally shown in FIGS. 3-4, body portion 101 may be of single-piece construction (e.g., may constitute a monolithic element). Depending on the orientation of navel retainer 100a, 100b when inserted within a navel, a given region of body portion 101 may be considered, for example, an upper body portion, lower body portion, or side body portion of navel retainer 100a, 100b, as the case may be. In some embodiments, a given region of body portion 101 optionally may be configured to host one or more intervening layers (e.g., coatings, bumpers, guides, sleeves, coverings, guards, etc.) which are to be disposed between the tissue of the navel and body portion 101. The material selection and dimensions of such optional intervening layer(s) may be customized, as desired for a given target application or end-use.

The dimensions and geometry of body portion 101 may be customized, as desired for a given target application or end-use. In accordance with some embodiments, a given body portion 102, 104 may be of generally rounded shape. For instance, a given body portion 102, 104 may be arcuate (e.g., semi-circular, semi-elliptical, open curve) or otherwise curved in shape and may have a substantially constant radius or a variable radius, as desired for a given target application or end-use. In some embodiments, navel retainer 100a may be configured such that, in its fully collapsed state, body portions 102, 104 interface in a manner that results in body portion 101 being of generally circular geometry. In some other embodiments, navel retainer 100a may be configured such that, in its fully collapsed state, body portions 102, 104 interface in a manner that results in body portion 101 being of generally elliptical, oval, oblate, prolate, or other curved geometry suitable to fit within a navel of a given size. In accordance with some embodiments, navel retainer 100a, 100b may be configured such that, in its fully collapsed state, its body portion 101 may be of a first geometry (e.g., a circular geometry), whereas in a partially or fully expanded state, its body portion 101 may be of a different second geometry (e.g., an elliptical geometry). As will be appreciated in light of this disclosure, in cases where body portion 101 is of single-piece construction, it may be of any of the various example geometries discussed above, for instance, with respect to a body portion 101 of multi-piece construction. Other suitable configurations for body portion 101 (e.g., with its one or more constituent body portions) will depend on a given application and will be apparent in light of this disclosure.

Navel retainer 100a also may include one or more brace portions 106, 108, which may be configured, in accordance with some embodiments, to provide a given degree of structural rigidity to navel retainer 100a and serve to operatively couple a given body portion 102, 104 with adjustment mechanism 112 (discussed below). In some embodiments, a given brace portion 106, 108 and its corresponding body portion 102, 104 may be of single-piece construction (e.g., may constitute a monolithic element), whereas in some other embodiments, they may be of multi-piece construction and assembled with one another (e.g., may constitute a polylithic element). The dimensions and geometry of a given brace portion 106, 108 may be customized, as desired for a given target application or end-use. In some cases, a given brace portion 106, 108 may be a substantially elongate, bar-like body, extending from a center portion 110 (discussed below) to a corresponding given body portion 102, 104. In some instances, a given brace portion 106, 108 may be of generally constant width along its length, whereas in some other instances, its width may vary along its length. For instance, as generally can be seen from FIG. 1, in some embodiments, a given brace portion 106, 108 may be of greater width (e.g., flared) at its distal end, which interfaces, directly or indirectly, with a corresponding body portion 102, 104, than at its proximal end, which interfaces, directly or indirectly, with center portion 110. Other suitable configurations for brace portions 106, 108 will depend on a given application and will be apparent in light of this disclosure.

As previously noted, navel retainer 100a may include a center portion 110, which may be disposed in a generally centered manner with respect to one or more axes of navel retainer 100a. In some cases, center portion 110 may be disposed substantially equidistantly from body portions 102, 104, though in some other cases, center portion 110 optionally may be disposed closer to one of body portions 102, 104 than the other. The geometry and dimensions of center portion 110 may be customized, as desired for a given target application or end-use. As discussed below, an adjustment mechanism 112 of navel retainer 100a may be disposed, in part or in whole, at center portion 110, in accordance with some embodiments. Other suitable configurations for center portion 110 will depend on a given application and will be apparent in light of this disclosure.

As previously noted, navel retainer 100a may include an adjustment mechanism 112 configured to provide for expansion and collapsing of the size (and, optionally, change in geometry) of body portion 101 along one or more axes. More specifically, adjustment mechanism 112 may be configured, in accordance with some embodiments, to advance and retract either (or both) brace portions 106, 108 and their attendant body portions 102, 104 in a linear or other desired manner with respect to center portion 110 (or other specified portion of navel retainer 100a). To such ends, adjustment mechanism 112 may be configured to generate movement in one or more directions based on mechanical, hydraulic, pneumatic, electronic, magnetic, or any other suitable force application means. For instance, in accordance with some embodiments, adjustment mechanism 112 may be any one, or combination, of a threaded screw-based mechanism, a spring-based mechanism, or a gear-based mechanism, among others.

In some embodiments, adjustment mechanism 112 may be configured to operate such that body portion 101 of navel retainer 100a may increase or decrease in size, as the case may be, in a smooth incremental manner. In some other embodiments, however, adjustment mechanism 112 may be configured to operate such that body portion 101 of navel retainer 100a may increase or decrease in size, as the case may be, in a stepwise or other non-smooth incremental manner. For instance, in an example case, adjustment mechanism 112 may be configured for ratchet-type adjustment, having one or more defined stopping points, the quantity and pitch of which may be customized, as desired for a given target application or end-use. In some embodiments, adjustment mechanism 112 may be configured to provide continuous adjustment of the size of body portion 101, whereas in some other embodiments, adjustment mechanism 112 may be configured to provide discontinuous adjustment of the size of body portion 101. Adjustment may be provided via any one, or combination, of manual or automated means, such as, for example, by hand, by tool, or by external device. Other suitable configurations for adjustment mechanism 112 will depend on a given application and will be apparent in light of this disclosure.

In at least some cases where body portion 101 is of multi-piece construction, its constituent body portions 102, 104 may be physically separated from one another by a gap 114. Similarly, in at least some cases where body portion 101 is of single-piece construction, body portion 101 may be discontinuous, being separated by a gap 114. As will be appreciated in light of this disclosure, the dimensions of a given gap 114 may change, for instance, depending on whether navel retainer 100a, 100b is in its fully collapsed state, fully expanded state, or some intermediate expanded state there between. In accordance with some embodiments, as adjustment mechanism 112 is operated to effectuate adjustment of the size (and, optionally, geometry) of navel retainer 100a, a given gap 114 may increase or decrease in size accordingly. As a given gap 114 approaches zero, body portions 102, 104 may come to interface, directly or indirectly, with one another. Other suitable configurations for gap(s) 114 will depend on a given application and will be apparent in light of this disclosure.

In accordance with some embodiments, navel retainer 100a, 100b optionally may include one or more biasing members 116, which may be disposed, in part or in whole, within a given gap 114, for instance, between body portions 102, 104. A given biasing member 116 may be configured, in accordance with some embodiments, to help maintain a given desired orientation and/or spacing between body portions 102, 104. In some embodiments, a given optional biasing member 116 may be a collapsible or extendable body configured to compress or stretch with the movement of body portions 102, 104 relative to one another. For example, a given biasing member 116 may be, in some cases, a spring, an elastomeric element, a piston, or a body capable of telescoping, to name a few. In some other embodiments, a given optional biasing member 116 may be a rigid (or semi-rigid) body that, rather than collapsing or extending, is configured to be hosted, in part or in whole, by a corresponding recess in either (or both) body portions 102, 104. To that end, a given biasing member 116 may be, for instance, a rod-type body of solid or hollow (e.g., tubular) configuration, and a corresponding recess may be provisioned such that the rod-type body may be inserted into and withdrawn from it with the movement of body portions 102, 104 relative to one another. Optionally, such a rod-type body and corresponding recess may be configured for threaded screw-like engagement, in accordance with some embodiments. Other suitable configurations for optional biasing member(s) 116 will depend on a given application and will be apparent in light of this disclosure.

In accordance with some embodiments, navel retainer 100a, 100b optionally may include one or more points of attachment for ornamentation, such as navel piercing jewelry or other navel adornments. For instance, in some embodiments, navel retainer 100a may include one or more central ornamentation mounting portions 118. A given central ornamentation mounting portion 118 may be provided, in part or in whole, at any one, or each, of brace portions 106, 108 and center portion 110. In some embodiments, navel retainer 100a may include one or more peripheral ornamentation mounting portions 120. A given peripheral ornamentation mounting portion 120 may be provided, in part or in whole, at either, or both, of body portions 102, 104 or, more generally, body portion 101. In cases where a plurality of ornamentation mounting portions 118, 120 are provided, the arrangement (e.g., quantity, spacing, orientation, and so forth) thereof may be customized, as desired for a given target application or end-use. Moreover, the geometry and dimensions of a given ornamentation mounting portion 118, 120 may be customized, as desired.

A given ornamentation mounting portion 118, 120 may be of any suitable configuration that allows for a given manner of ornamentation to be mounted thereat in a temporary or permanent manner, as desired. The specific means by which a given ornamentation mounting portion 118, 120 may provide for mounting of ornamentation thereat may be customized, as desired for a given target application or end-use, and in at least some cases may be configured as typically done for mounting of jewelry and adornments. Some example suitable mounting means may include, for instance, snap, magnetic, clip, buckle, hook-and-loop, adhesive, bayonet-type, and threaded screw-type mounting elements, to name a few. Of course, as will be appreciated in light of this disclosure, navel retainer 100a, 100b additionally or alternatively may include one or more integrated ornamentations and is not intended to be limited only to attachable/detachable ornamentations. Other suitable configurations for ornamentation mounting portion(s) 118, 120 will depend on a given application and will be apparent in light of this disclosure.

Navel retainer 100a, 100b may be constructed from any of a wide range of materials, any of which optionally may be medical-grade. For example, in some embodiments, navel retainer 100a, 100b may be constructed, in part or in whole, from a metal or alloy, such as a stainless steel (e.g., a surgical stainless steel), gold, silver, or platinum, to name a few. In some embodiments, navel retainer 100a, 100b may be constructed, in part or in whole, from an elastomeric or polymeric material (e.g., such as a plastic, rubber, or silicone), a ceramic material, a composite material, a mineral material, a glass material, or a wooden material, among others. As will be appreciated in light of this disclosure, the selection of different construction materials may allow for navel retainer 100a, 100b to have sufficient rigidity and/or softness (e.g., flexibility) to achieve desired navel shape and size characteristics for a user. In some instances, body portion 101 may be a rigid body, whereas in some other instances, it may be a semi-rigid or flexible body. The dimensions $D_1$-$D_8$ (e.g., height, width, length, diameter, radius, thickness, etc.) of various portions of navel retainer 100a, 100b may be customized, as desired for a given target application or end-use. In addition, the coloration of a given portion of navel retainer 100a, 100b may be customized, as desired. Other suitable configurations for navel retainer 100a, 100b will depend on a given application and will be apparent in light of this disclosure.

In accordance with some embodiments, navel retainer 100a, 100b may be configured to be expandable and collapsible to adjust its size and/or geometry. In the fully collapsed state of navel retainer 100a, 100b, body portion 101 may be characterizable as having its minimum possible size (e.g., smallest possible diameter/width or other dimension). In the fully expanded state of navel retainer 100a, 100b, body portion 101 may be characterizable as having its maximum possible size (e.g., largest possible diameter/width or other dimension). In accordance with some embodiments, navel retainer 100a, 100b further may be configured with one or more partially expanded states in which body portion 101 may be characterizable as having an intermediate size somewhere between its minimum and maximum possible sizes. Also, as previously noted, in adjusting the size of body portion 101, the overall geometry of navel retainer 100a, 100b may change as well, at least in some cases.

In accordance with some embodiments, adjustment mechanism 112 may be configured to transition navel retainer 100a between any of its various states, changing the size and/or geometry of body portion 101. As body portion 101 may interface, directly or indirectly, with tissue within the navel when navel retainer 100a, 100b is deployed therein, adjustment of the size and/or geometry of body portion 101 accordingly may alter the size and/or shape of the surrounding navel. In this manner, the native adjustability of navel retainer 100a, 100b may be utilized, in accordance with some embodiments, to adjust or maintain the size and/or shape of the host navel, for example, during a healing period or as otherwise desired.

Figure 5:
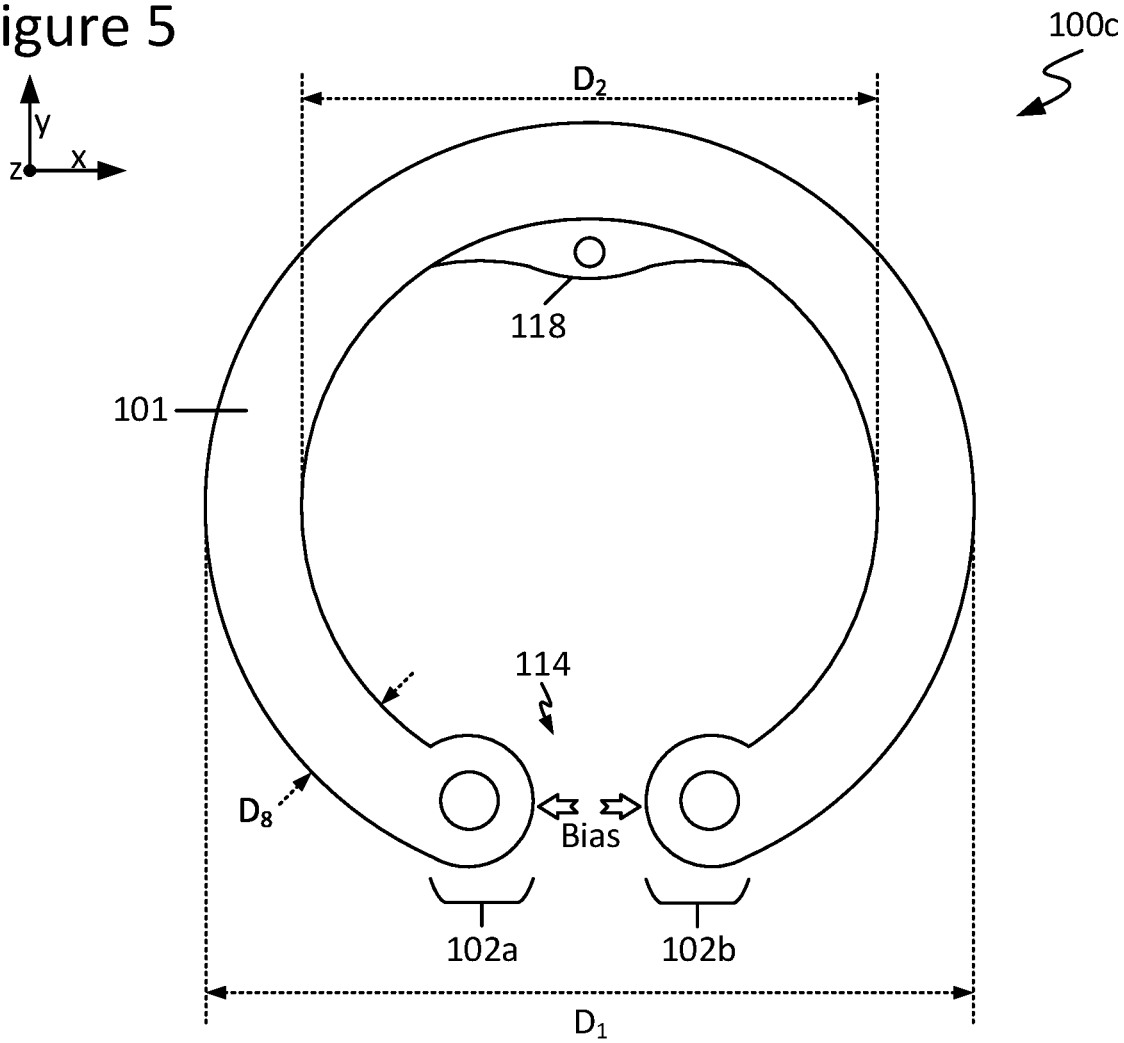
FIG. 5 illustrates a side elevation view of a navel retainer configured in accordance with another embodiment of the present disclosure.
Figure 6:
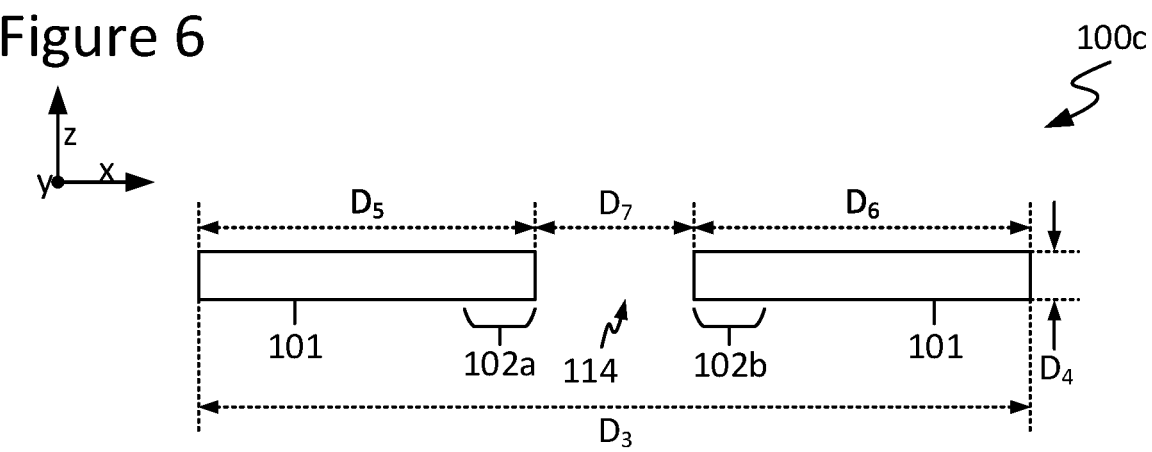
FIG. 6 illustrates an end view of the navel retainer of FIG. 5.

FIGS. 5-6 illustrate several views of a navel retainer 100c configured in accordance with another embodiment of the present disclosure. As can be seen, navel retainer 100c may include a body portion 101 having a first end portion 102a and an opposing second end portion 102b and may be configured to interface, directly or indirectly, with the interior sidewalls of a navel. In some embodiments, such as that generally shown in FIG. 5, body portion 101 may be of single-piece construction (e.g., may constitute a monolithic element). In some other embodiments, however, body portion 101 may be of multi-piece construction (e.g., may constitute a polylithic element). Depending on the orientation of navel retainer 100c when inserted within a navel, a given region of body portion 101 may be considered, for example, an upper body portion, lower body portion, or side body portion of navel retainer 100c, as the case may be. In some embodiments, a given region of body portion 101 optionally may be configured to host one or more intervening layers (e.g., coatings, bumpers, guides, sleeves, coverings, guards, etc.) which are to be disposed between the tissue of the navel and body portion 101. The material selection and dimensions of such optional intervening layer(s) may be customized, as desired for a given target application or end-use.

In accordance with some embodiments, navel retainer 100c may be configured such that its body portion 101 may compress and expand in size (and, optionally, change in geometry) along one or more axes. To that end, body portion 101 may be configured, in accordance with some embodiments, as a resilient element, characterizable as tending to recoil or spring back into shape despite being compressed or otherwise deflected from an undisturbed state. By virtue of its configuration, navel retainer 100c may permit temporary reduction of the size of body portion 101 when acted upon by a compressive force of sufficient magnitude. In the weakening or absence of such a compressive force, a restorative force of body portion 101 may tend to expand the size of body portion 101. Thus, by virtue of its configuration, body portion 101 may provide navel retainer 100c, in a general sense, with a spring-based adjustment mechanism. The degree of resilience may be customized by adjusting various characteristics of body portion 101, such as its material construction, geometry, and dimensions, for example.

Regarding material construction, navel retainer 100c may be constructed from any of the various example materials discussed above, for instance, with respect to navel retainer 100a, 100b in accordance with some embodiments. As will be appreciated in light of this disclosure, the selection of different construction materials may allow for navel retainer 100c to have sufficient resilience permitting flexibility for compression thereof yet also providing a sufficient restorative force causing body portion 101 to press against the tissue of a host navel to achieve desired navel shape and size characteristics for a user. In addition, the coloration of a given portion of navel retainer 100c may be customized, as desired.

Regarding geometry, body portion 101 may be of generally rounded shape, in accordance with some embodiments. For instance, body portion 101 may be arcuate (e.g., semicircular, semi-elliptical, open curve) or otherwise curved in shape and may have a substantially constant radius or a variable radius, as desired for a given target application or end-use. As can be seen from FIG. 1, for example, body portion 101 may be discontinuous, such that its end portions 102a, 102b are physically separated from one another by a gap 114.

As will be appreciated in light of this disclosure, the dimensions of gap 114 may change, for instance, depending on whether navel retainer 100c is in its fully compressed state, fully expanded state, or some intermediate expanded state there between. In accordance with some embodiments, as body portion 101 is compressed or allowed to expand to effectuate adjustment of the size (and, optionally, geometry) of navel retainer 100c, gap 114 may increase or decrease in size accordingly. As gap 114 approaches zero, end portions 102a, 102b may come to be adjacent one another and perhaps interface, directly or indirectly, with one another, at least in a temporary manner. In some cases, body portion 101 may be collapsed manually or with the use of a separate tool. The restorative force of body portion 101 may tend to bias end portions 102a, 102b away from one another, increasing the size of gap 114 and producing an overall increase in the size of body portion 101.

In some embodiments, navel retainer 100c may be configured such that, in its fully compressed state, end portions 102a, 102b may interface (or otherwise be proximate one another) in a manner that results in body portion 101 being of generally circular geometry. In some other embodiments, navel retainer 100c may be configured such that, in its fully compressed state, end portions 102a, 102b may interface (or otherwise be proximate one another) in a manner that results in body portion 101 being of generally elliptical, oval, oblate, prolate, or other curved geometry suitable to fit within a navel of a given size. In accordance with some embodiments, navel retainer 100c may be configured such that, in its fully compressed state, its body portion 101 may be of a first geometry (e.g., a circular geometry), whereas in a partially or fully expanded state, its body portion 101 may be of a different second geometry (e.g., an elliptical geometry).

Regarding dimensions, the dimensions $D_1$-$D_8$ (e.g., height, width, length, diameter, radius, thickness, etc.) of various portions of navel retainer 100c may be customized, as desired for a given target application or end-use. As will be appreciated in light of this disclosure, it may be desirable to ensure that the dimensions of a given region of body portion 101 are sufficiently large or small, as the case may be, to provide for a given target degree of resilience. Other suitable materials, geometries, and dimensions for body portion 101 will depend on a given application and will be apparent in light of this disclosure.

In accordance with some embodiments, navel retainer 100c optionally may include one or more points of attachment for ornamentation, such as navel piercing jewelry or other navel adornments. For instance, in some embodiments, navel retainer 100c may include one or more ornamentation mounting portions 118. In cases where a plurality of ornamentation mounting portions 118 are provided, the arrangement (e.g., quantity, spacing, orientation, and so forth) thereof may be customized, as desired for a given target application or end-use. Moreover, the geometry and dimensions of a given ornamentation mounting portion 118 may be customized, as desired.

A given ornamentation mounting portion 118 may be of any suitable configuration that allows for a given manner of ornamentation to be mounted thereat in a temporary or permanent manner, as desired. The specific means by which a given ornamentation mounting portion 118 may provide for mounting of ornamentation thereat may be customized, as desired for a given target application or end-use, and in at least some cases may be configured as typically done for mounting of jewelry and adornments. Some example suitable mounting means may include, for instance, snap, magnetic, clip, buckle, hook-and-loop, adhesive, bayonet-type, and threaded screw-type mounting elements, to name a few. Of course, as will be appreciated in light of this disclosure, navel retainer 100c additionally or alternatively may include one or more integrated ornamentations and is not intended to be limited only to attachable/detachable ornamentations. Other suitable configurations for ornamentation mounting portion(s) 118 will depend on a given application and will be apparent in light of this disclosure.

In accordance with some embodiments, navel retainer 100c may be configured to be expandable and compressible to adjust its size and/or geometry. In the fully compressed state of navel retainer 100c, body portion 101 may be characterizable as having its minimum possible size (e.g., smallest possible diameter/width or other dimension). In the fully expanded state of navel retainer 100c, body portion 101 may be characterizable as having its maximum possible size (e.g., largest possible diameter/width or other dimension). In accordance with some embodiments, navel retainer 100c further may be configured with one or more partially expanded states in which body portion 101 may be characterizable as having an intermediate size somewhere between its minimum and maximum possible sizes. Also, as previously noted, in adjusting the size of body portion 101, the overall geometry of navel retainer 100c may change as well, at least in some cases.

In accordance with some embodiments, the restorative force exerted by virtue of the configuration of body portion 101 may serve to transition navel retainer 100c between any of its various states, changing the size and/or geometry of body portion 101. As body portion 101 may interface, directly or indirectly, with tissue within the navel when navel retainer 100c is deployed therein, adjustment of the size and/or geometry of body portion 101 accordingly may alter the size and/or shape of the surrounding navel. In this manner, the native adjustability of navel retainer 100c may be utilized, in accordance with some embodiments, to adjust or maintain the size and/or shape of the host navel, for example, during a healing period or as otherwise desired.

Methodologies

Figure 7:
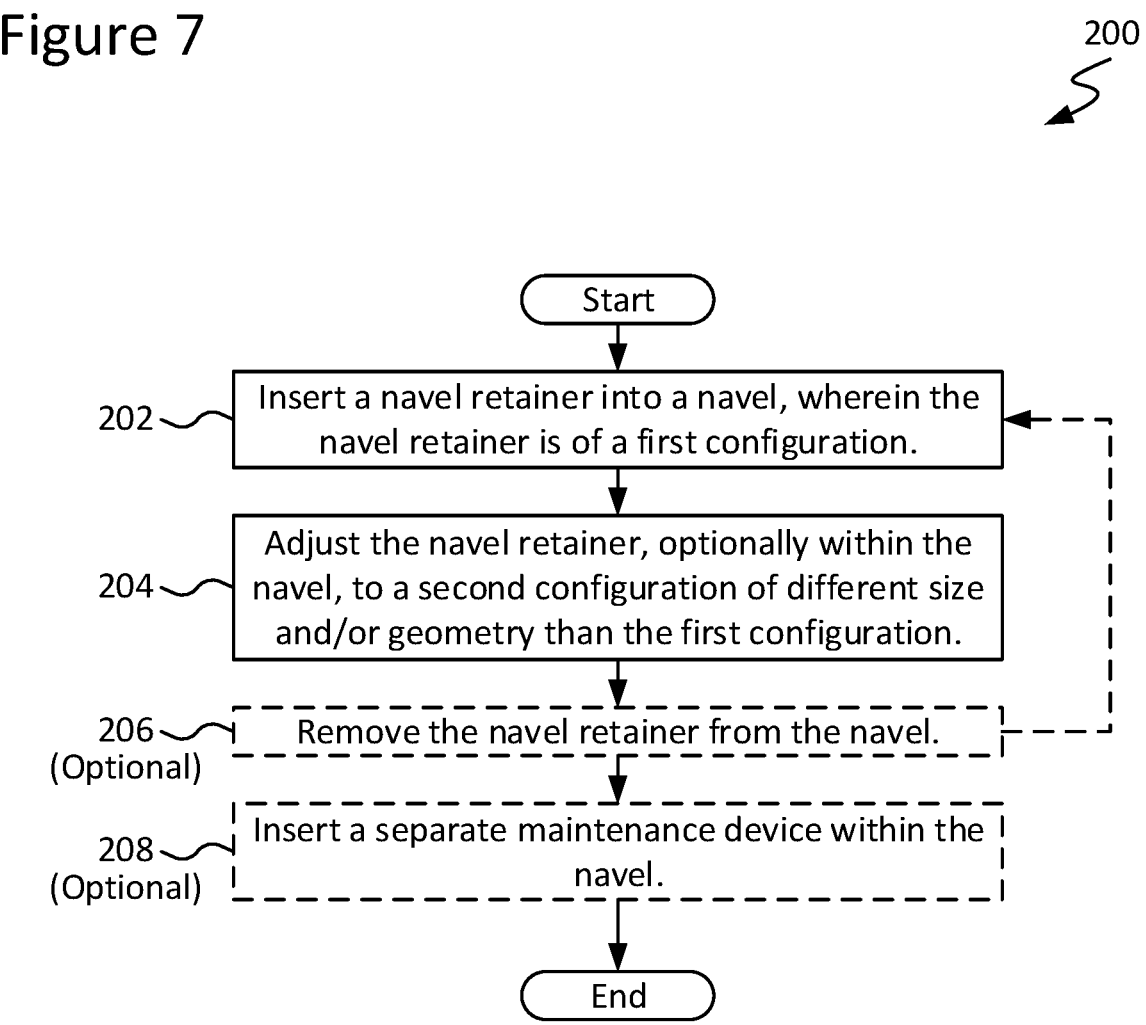
FIG. 7 is a flowchart illustrating a method of using a navel retainer in accordance with an embodiment of the present disclosure.

FIG. 7 is a flowchart illustrating a method 200 of using a navel retainer in accordance with an embodiment of the present disclosure. Method 200 may be utilized, in accordance with some embodiments, in combating contracture of a navel, for example, during a healing period. Method 200 may begin as in block 202 with inserting a navel retainer into a navel, wherein the navel retainer is of a first configuration. In an example case, the navel retainer may be, for instance, either navel retainer 100a or 100b, described herein. The first configuration may be characterized as being of a given first size and geometry. When inserted, the body portion of the navel retainer may interface, directly or indirectly, with the sidewall tissue (or other tissue) within the navel. The snugness of the fit achieved in such initial insertion may be of a greater or lesser degree, as the case may be, but may change with adjustment of the size and/or geometry of the navel retainer, as discussed further below.

Method 200 may continue as in block 204 with adjusting the navel retainer, optionally within the navel, to a second configuration of different size and/or geometry than the first configuration. In an example case, adjustment may be provided, for instance, via adjustment mechanism 112, described herein. In performing such adjustment, the body portion of the navel retainer may increase or decrease in size and, optionally, may change in geometry. In this manner, the snugness of the fit of the navel retainer may change, and the body portion may come to exert a greater or lesser pressure on tissue within the host navel than may be present during the initial insertion (block 202).

Method 200 optionally may continue as in block 206 with removing the navel retainer from the navel. In some cases, it may be desirable to adjust (e.g., reduce) the size of the navel retainer prior to attempting removal, though in at least some instances, no such adjustment may be needed to effectuate removal. Optionally, after removing the navel retainer, method 200 may return to block 202, the navel retainer being reinserted within the navel (e.g., such as may be performed after cleaning the navel retainer and/or checking on the condition of the navel during the healing process).

Method 200 optionally may continue as in block 208 with inserting a separate maintenance device within the navel. Thus, if the navel retainer of blocks 202-206 is configured as the navel retainer 100a of FIGS. 1-2, then the separate maintenance device may be configured, in accordance with some embodiments, as the navel retainer 100b of FIGS. 3-4. The maintenance device may be employed once the desired navel size and shape are obtained and may be used on a temporary or perpetual basis.

As will be appreciated in light of this disclosure, the amount of time that may be allowed to elapse between any of insertion (block 202), adjustment (block 204), optional removal (block 206), and optional insertion for maintenance (block 208) may be customized, as desired for a given target application or end-use. It should be noted that any of these various periods need not be strictly continuous, as the navel retainer or the separate maintenance device, as the case may be, may be removed temporarily or as otherwise desired, for instance, to permit cleaning or other upkeep or inspection of the host navel and such devices.

FIG. 8 is a flowchart illustrating a method 300 of using a navel retainer in accordance with another embodiment of the present disclosure. Method 300 may be utilized, in accordance with some embodiments, in combating contracture of a navel, for example, during a healing period. Method 300 may begin as in block 302 with inserting a navel retainer into a navel, wherein the navel retainer is of a first compressed configuration. In an example case, the navel retainer may be, for instance, navel retainer 100c, described herein. The first configuration may be characterized as being of a given first size and geometry. When inserted, the body portion of the navel retainer may interface, directly or indirectly, with the sidewall tissue (or other tissue) within the navel. The snugness of the fit achieved in such initial insertion may be of a greater or lesser degree, as the case may be, but may change with adjustment of the size and/or geometry of the navel retainer, as discussed further below.

Method 300 may continue as in block 304 with allowing the navel retainer to expand, optionally within the navel, to a second expanded configuration of different size and/or geometry than the first compressed configuration. In an example case, expansion may result from the resilience of body portion 101, described herein. In allowing such adjustment, the body portion of the navel retainer may increase in size and, optionally, may change in geometry. In this manner, the snugness of the fit of the navel retainer may change, and the body portion may come to exert a greater or lesser pressure on tissue within the host navel than may be present during the initial insertion (block 302).

Method 200 optionally may continue as in block 306 with removing the navel retainer from the navel. In some cases, it may be desirable to compress (e.g., reduce) the size of the navel retainer prior to attempting removal, though in at least some instances, no such adjustment may be needed to effectuate removal. Optionally, after removing the navel retainer, method 300 may return to block 302, the navel retainer being reinserted within the navel (e.g., such as may be performed after cleaning the navel retainer and/or checking on the condition of the navel during the healing process).

Method 300 optionally may continue as in block 308 with inserting a separate maintenance device within the navel. The maintenance device may be employed once the desired navel size and shape are obtained and may be used on a temporary or perpetual basis.

As will be appreciated in light of this disclosure, the amount of time that may be allowed to elapse between any of insertion (block 302), expansion (block 304), optional removal (block 306), and optional insertion for maintenance (block 308) may be customized, as desired for a given target application or end-use. It should be noted that any of these various periods need not be strictly continuous, as the navel retainer or the separate maintenance device, as the case may be, may be removed temporarily or as otherwise desired, for instance, to permit cleaning or other upkeep or inspection of the host navel and such devices.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description. Future-filed applications claiming priority to this application may claim the disclosed subject matter in a different manner and generally may include any set of one or more limitations as variously disclosed or otherwise demonstrated herein.

What is claimed is:

1. A navel retainer device comprising:
a resilient body portion of open curve geometry having a gap defined therein such that the resilient body portion is discontinuous, wherein:
the resilient body portion includes:
a first face;
a second face situated opposite the first face; and
an outer circumferential surface that extends between the first face and the second face and is substantially perpendicular thereto;
a first end of the resilient body portion transitions to a first end portion that extends toward the gap, wherein the first end portion has a first recess formed therein which extends through the first face;
a second end of the resilient body portion transitions to a second end portion that extends toward the gap, wherein the second end portion has a second recess formed therein which extends through the first face;
the resilient body portion is configured to be inserted within a navel such that the outer circumferential surface of the resilient body portion interfaces with interior sidewall tissue of the navel hosting the navel retainer device; and
the resilient body portion is configured to resist compression of a size thereof as well as to exert pressure on the interior sidewall tissue in a manner that resists contracture of the navel.

2. The navel retainer device of claim 1, wherein the resilient body portion is configured such that, in a fully collapsed state of the navel retainer device, the resilient body portion is of substantially circular, elliptical, oval, oblate, or prolate geometry.

3. The navel retainer device of claim 1, further comprising an ornamentation mounting portion configured to mount navel ornamentation, wherein the ornamentation mounting portion is positioned distally from the gap.

4. The navel retainer device of claim 3, further comprising an ornamentation hosted by the ornamentation mounting portion of the navel retainer device.

5. The navel retainer device of claim 3, wherein the ornamentation mounting portion extends radially inward from an inner circumferential surface of the resilient body portion, wherein the ornamentation mounting portion and the resilient body portion together are of single-piece construction.

6. The navel retainer device of claim 1, further comprising a layer disposed on the resilient body portion and configured to intervene between the resilient body portion and the interior sidewall tissue of the navel, wherein the layer comprises at least one of a coating, a bumper, a guide, a sleeve, a covering, and a guard.

7. The navel retainer device of claim 1, wherein:
in a fully collapsed state of the navel retainer device, the resilient body portion is of a first geometry; and
in a fully expanded state of the navel retainer device, the resilient body portion is of a second geometry which differs from the first geometry.

8. The navel retainer device of claim 1, wherein the resilient body portion is comprised of a metal or alloy.

9. The navel retainer device of claim 1, wherein the resilient body portion is comprised of at least one of an elastomeric material, a polymeric material, a rubber, and a silicone.

10. The navel retainer device of claim 1, wherein the navel retainer device is configured to be adjusted in size manually.

11. The navel retainer device of claim 1, wherein the navel retainer device is configured to be adjusted in size utilizing a separate tool.

12. The navel retainer device of claim 1, wherein the resilient body portion is of substantially rectangular cross-section as taken in a transverse direction through the first face and the second face.

13. The navel retainer device of claim 1, wherein:
the first end portion extends toward the gap in a convexly rounded manner; and
the second end portion extends toward the gap in a convexly rounded manner.

14. The navel retainer device of claim 13, wherein in a radial direction with respect to the resilient body portion, at least one of:
the first end portion is of a greater dimension than the first end; and
the second end portion is of a greater dimension than the second end.

15. The navel retainer device of claim 13, wherein the resilient body portion is configured to be inserted within the navel such that the entire outer circumferential surface of the resilient body portion, from the first end portion to the second end portion, interfaces either:
directly with interior sidewall tissue; or
indirectly with interior sidewall tissue via an intervening material layer.

16. The navel retainer device of claim 13, wherein at least one of:
the first end portion extends further radially inward toward a center of the navel retainer device than the corresponding first end; and
the second end portion extends further radially inward toward the center of the navel retainer device than the corresponding second end.

17. The navel retainer device of claim 1, wherein at least one of the first face and the second face is substantially flat.

18. The navel retainer device of claim 1, wherein:
both the first face and the second face are substantially flat; and
the first face and the second face extend substantially parallel to each other.

19. The navel retainer device of claim 1, wherein the first recess and the second recess extend through the first face substantially parallel to each other.

20. The navel retainer device of claim 1, wherein the first recess and the second recess also extend through the second face.

* * * * *